United States Patent [19]

Muto et al.

[11] Patent Number: 5,032,074
[45] Date of Patent: Jul. 16, 1991

[54] APPARATUS FOR MANUFACTURING HARD CAPSULES FOR MEDICAMENT USE

[75] Inventors: Hiroaki Muto, Joetu; Yuichi Nishiyama, Kubiki; Toru Chiba, Joetu; Kiyoshi Araume, Iwatsuki, all of Japan

[73] Assignee: Shin-Etsu Chemical Co., Ltd., Japan

[21] Appl. No.: 485,835

[22] Filed: Feb. 28, 1990

Related U.S. Application Data

[60] Continuation of Ser. No. 114,715, Oct. 30, 1987, abandoned, which is a division of Ser. No. 46,433, May 6, 1987, abandoned.

[30] Foreign Application Priority Data

May 12, 1986 [JP] Japan .................................. 61-108275
Nov. 17, 1986 [JP] Japan .................................. 61-274781

[51] Int. Cl.[5] ............................................. B29C 41/14
[52] U.S. Cl. .................................. 425/272; 118/423; 425/93; 425/274; 425/804
[58] Field of Search ................ 425/269, 270, 272, 274, 425/275, 804, 93, 96; 264/301, 297.8, 303–307, DIG. 37; 536/99; 118/423, 425; 106/170, 181, 189

[56] References Cited

U.S. PATENT DOCUMENTS

| | | | |
|---|---|---|---|
| 1,657,982 | 1/1928 | Wilkie et al. | 264/307 X |
| 1,787,777 | 1/1931 | Colton | 425/96 |
| 1,831,212 | 11/1931 | Voss et al. | 264/307 X |
| 1,870,775 | 8/1932 | Gammeter | 264/304 X |
| 2,217,213 | 10/1940 | Bratring | 425/274 |
| 2,526,683 | 10/1950 | Murphy | 106/189 X |
| 2,575,789 | 11/1951 | Bogin | 425/274 X |
| 2,810,659 | 10/1957 | Greminger, Jr. et al. | 106/181 |
| 3,493,407 | 2/1970 | Greminger, Jr. et al. | 264/301 X |
| 3,617,588 | 11/1971 | Langman | 264/301 X |
| 3,794,453 | 2/1974 | Padilla et al. | 425/270 |
| 4,001,211 | 1/1977 | Sarkar | 106/170 X |

FOREIGN PATENT DOCUMENTS

056825 8/1982 European Pat. Off. .
180287 5/1986 European Pat. Off. .

*Primary Examiner*—Richard L. Chiesa
*Attorney, Agent, or Firm*—Parkhurst, Wendel & Rossi

[57] ABSTRACT

An apparatus for manufacturing capsules which causes a solution of thermo-gelling material to gelatinize, and then drys the gel, whereby the process of manufacturing capsules is less affected by drying conditions, thus providing capsules of uniform wall thickness without wrinkles. In the apparatus of this invention, circulating capsule pins are dipped in the solution of thermo-gelling material, thus the solution adheres to the pins, and, the pins are rotated upside down, thus thickness of the solution adhering to the pins becomes uniform. Then, the pins are retained in the vessel maintained at a higher temperature than the gelling temperature of the solution, and the solution adhering to the pins is accelerated to gelatinization. The formed gel is dried in a drying device, and the dried gel bodies, i.e. capsules, are removed from the capsule pins.

7 Claims, 15 Drawing Sheets

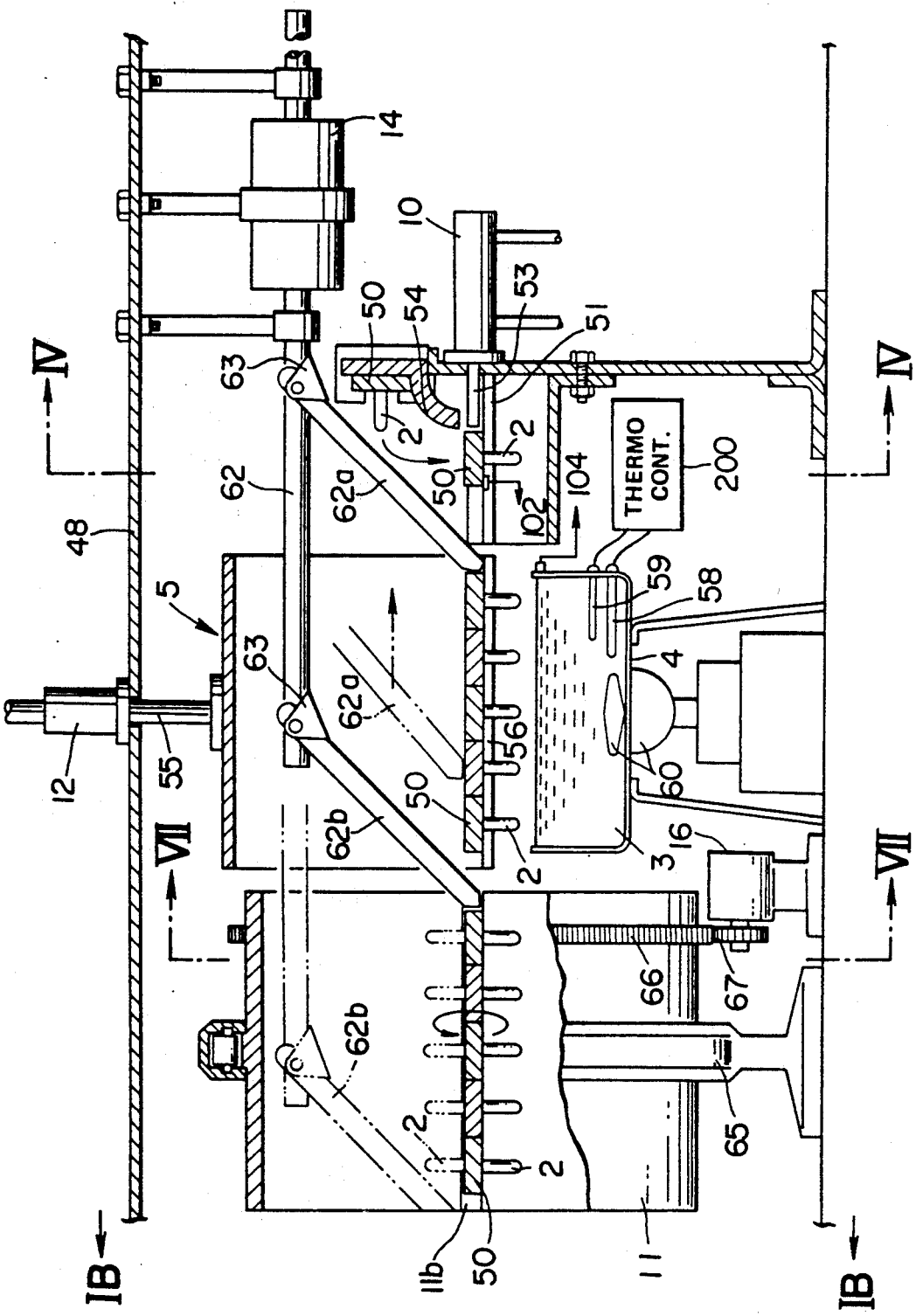
FIG.1A IA-IA

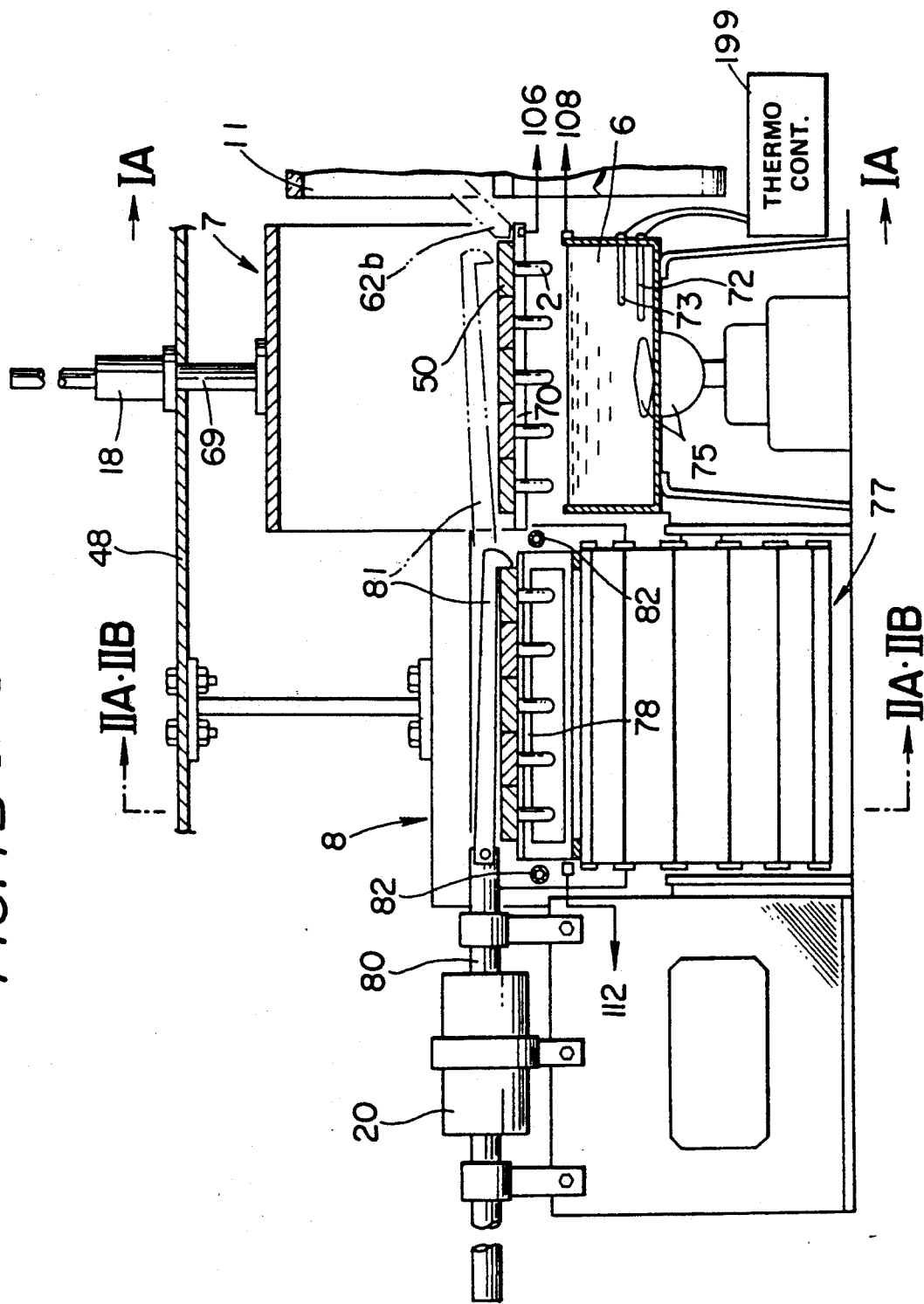

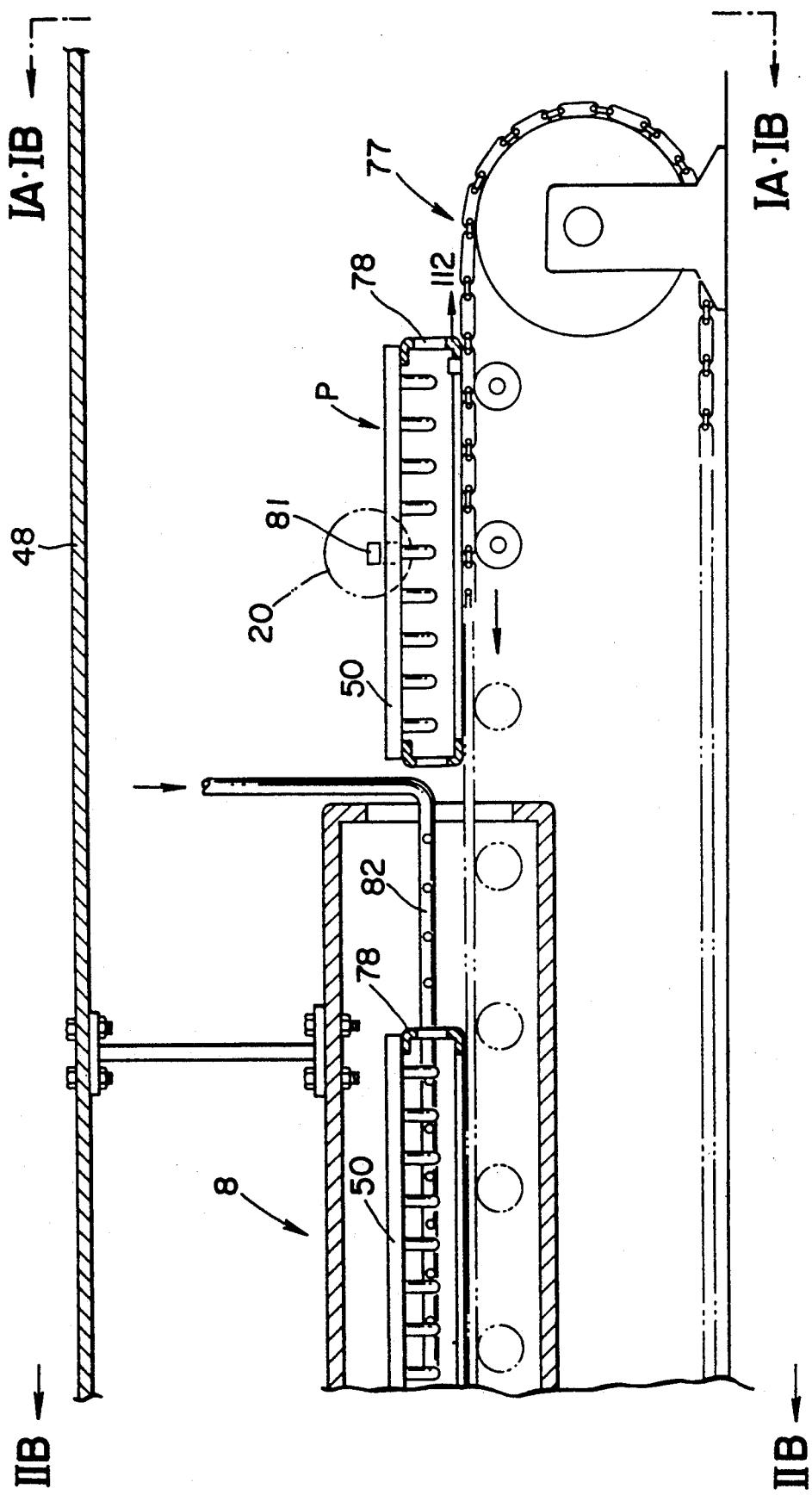

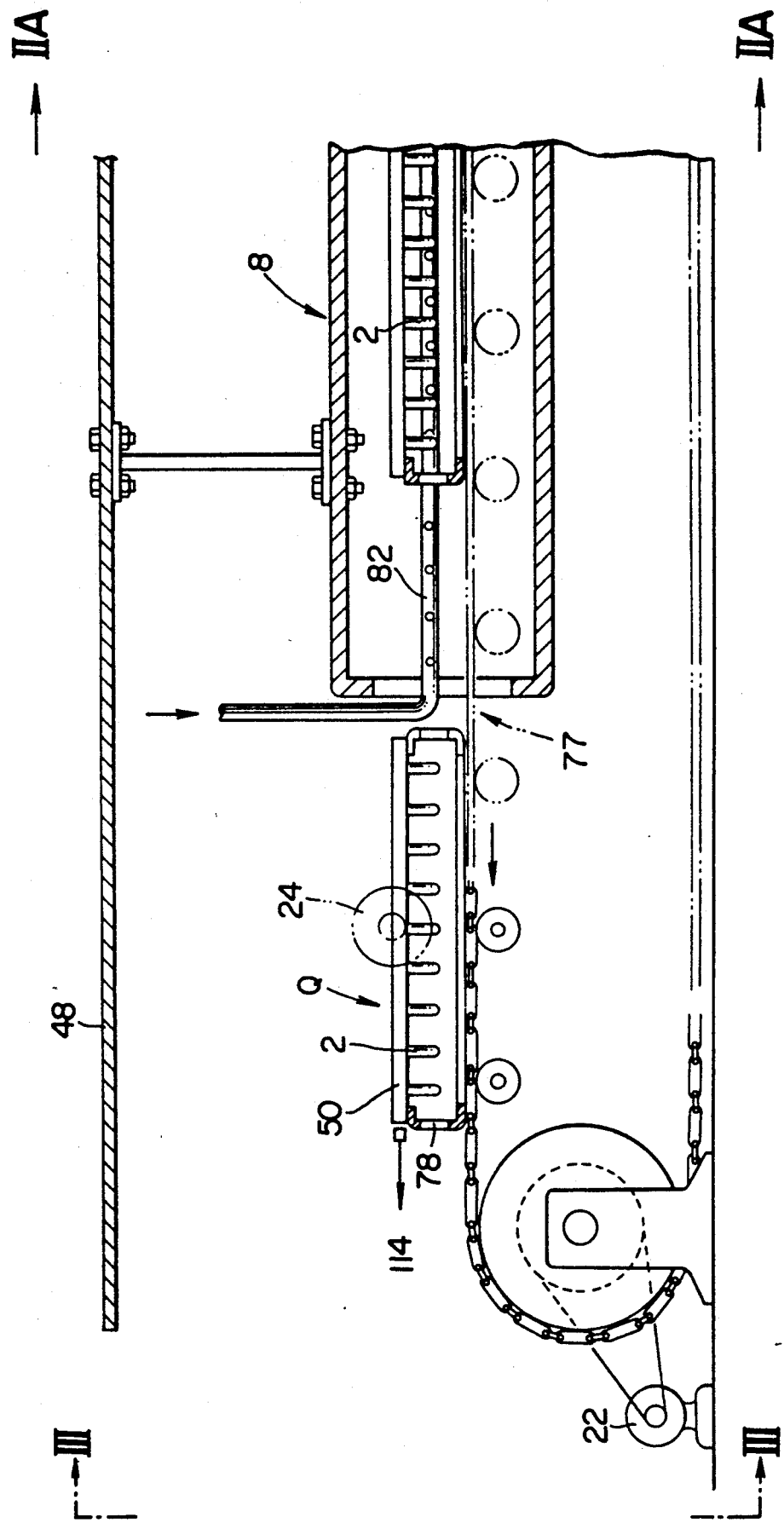

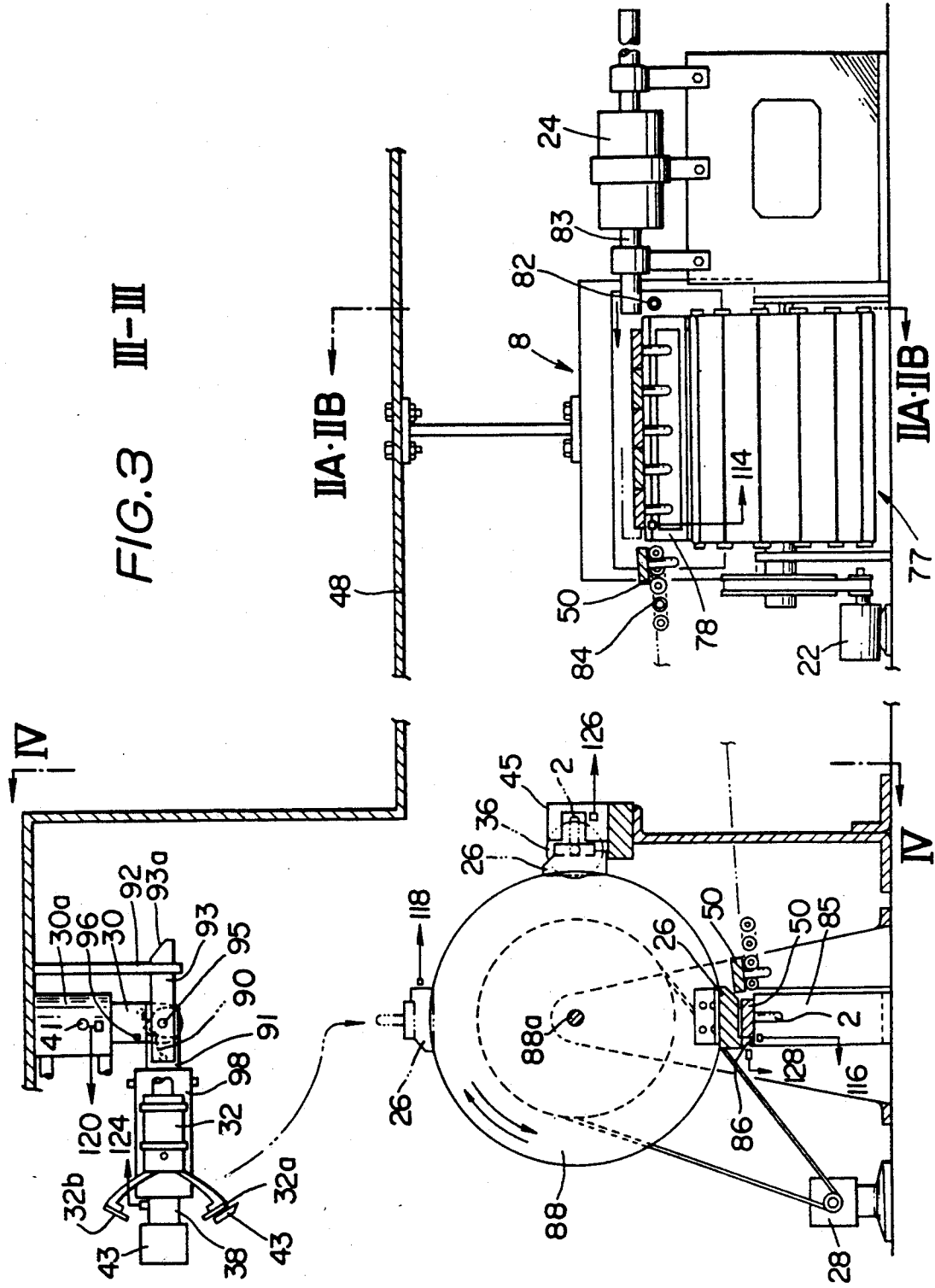

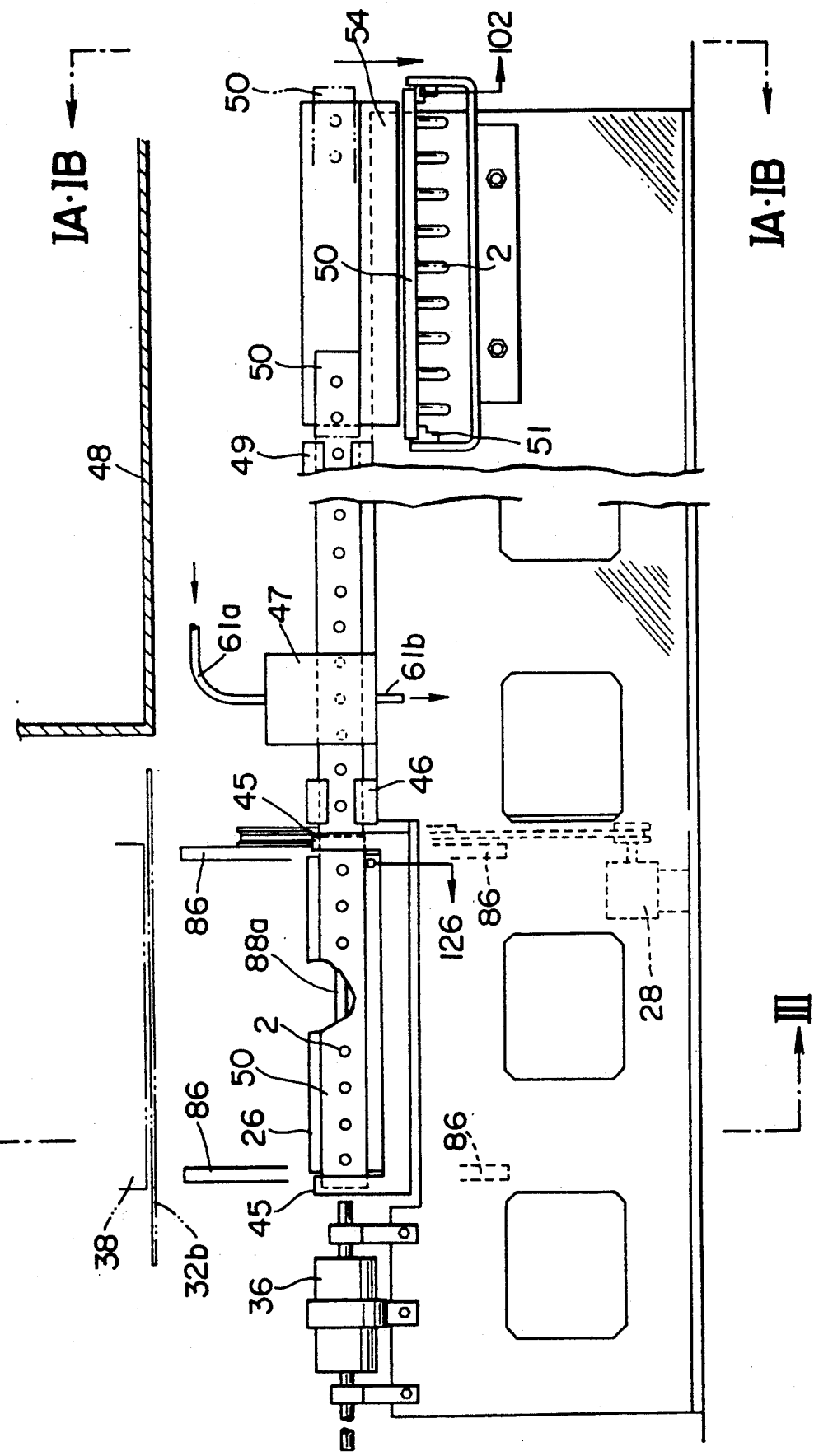

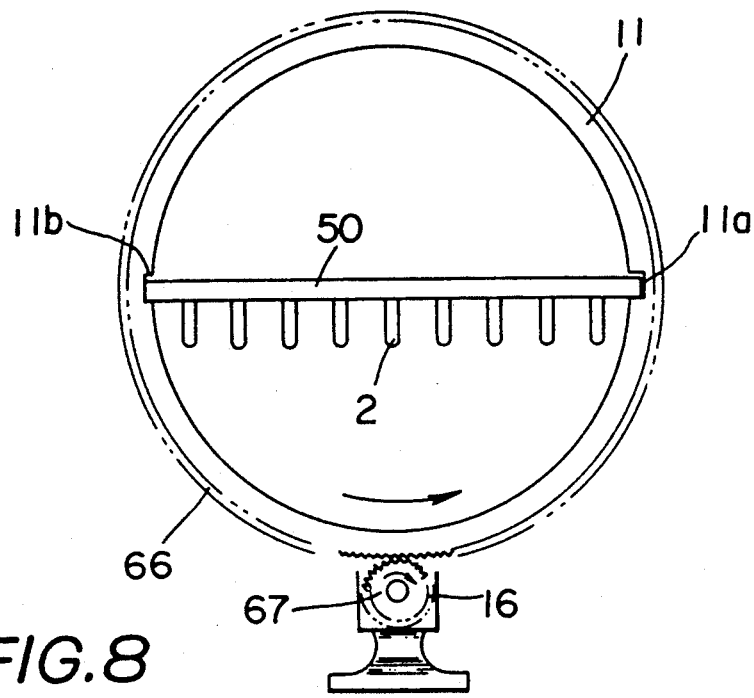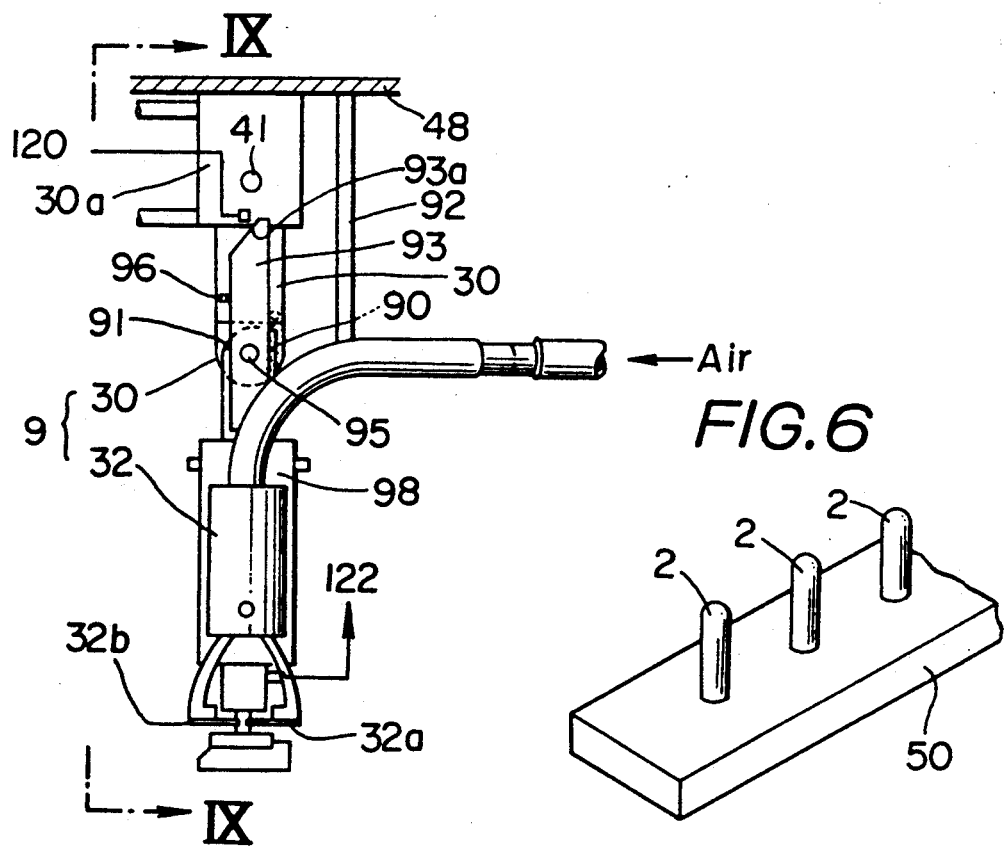

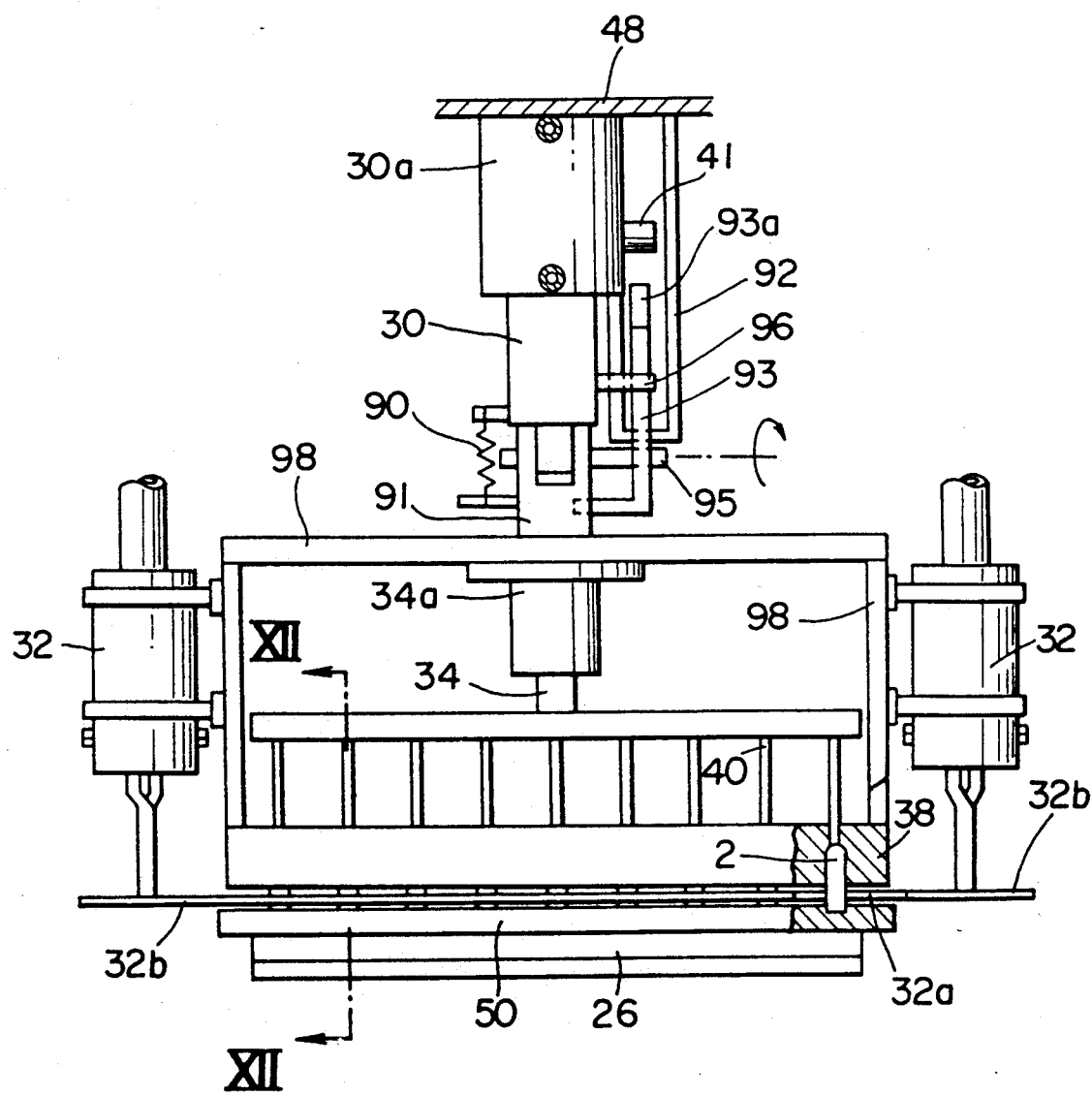

FIG. 10
FIG. 12 XII-XII
FIG. 11
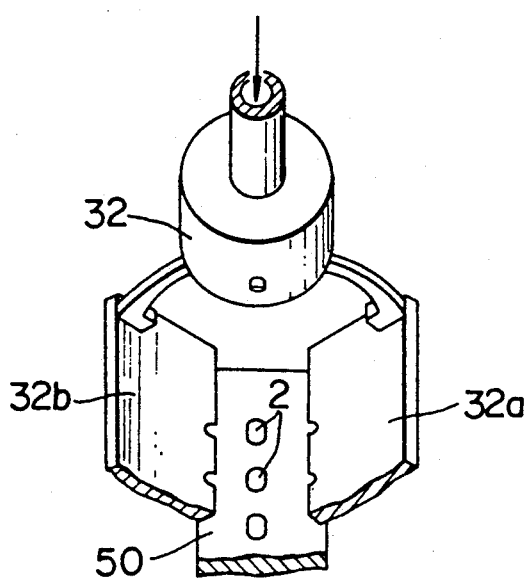
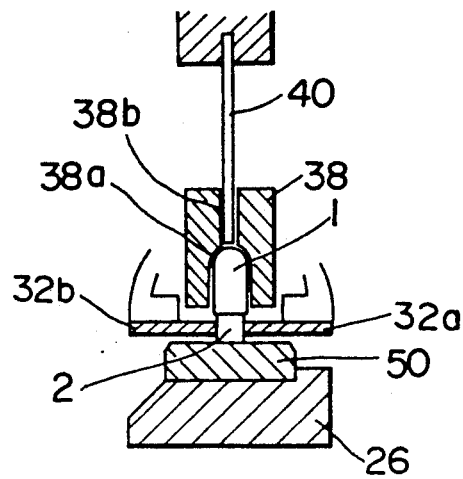
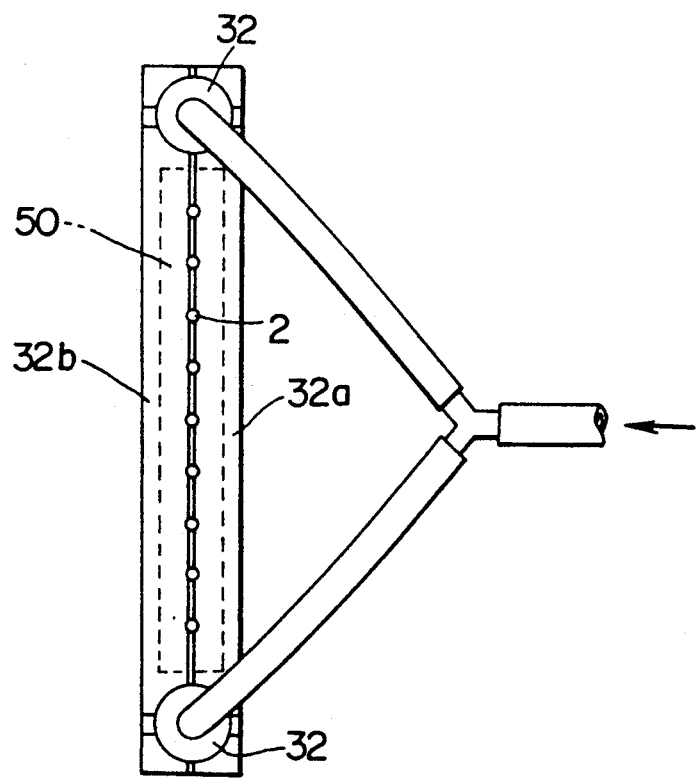

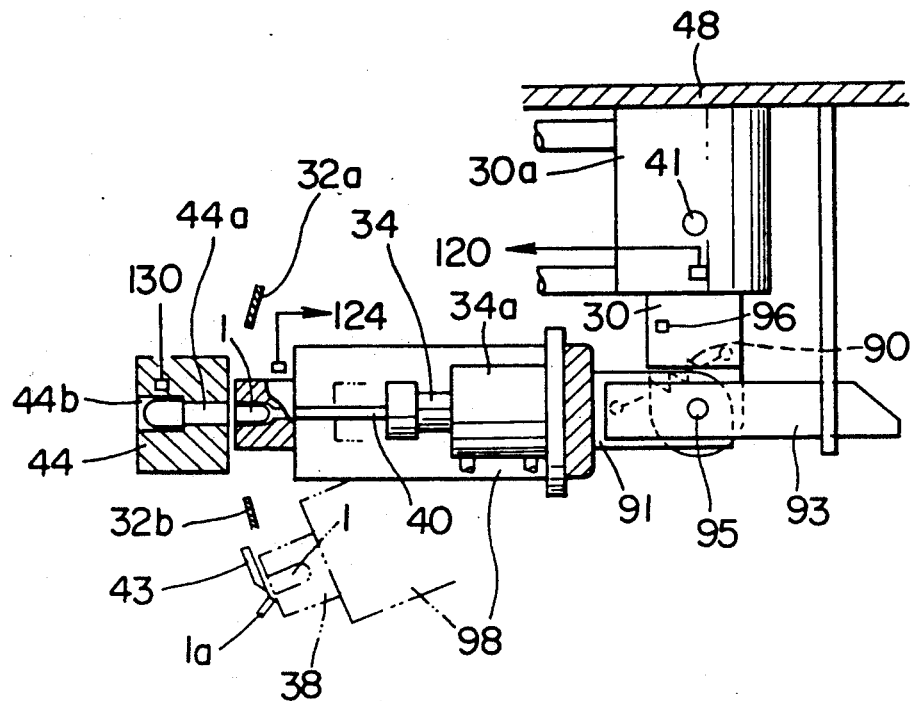
FIG.13
FIG.14
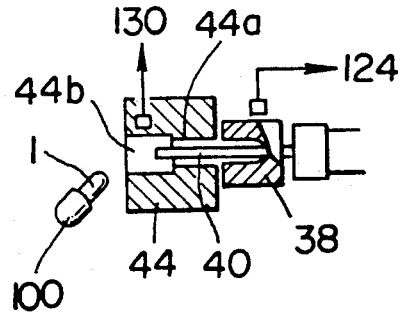
FIG.15
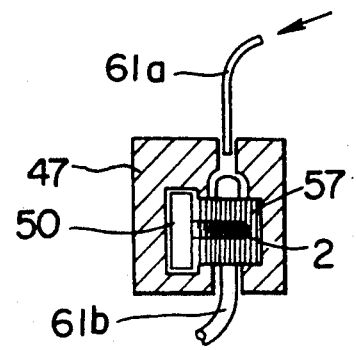

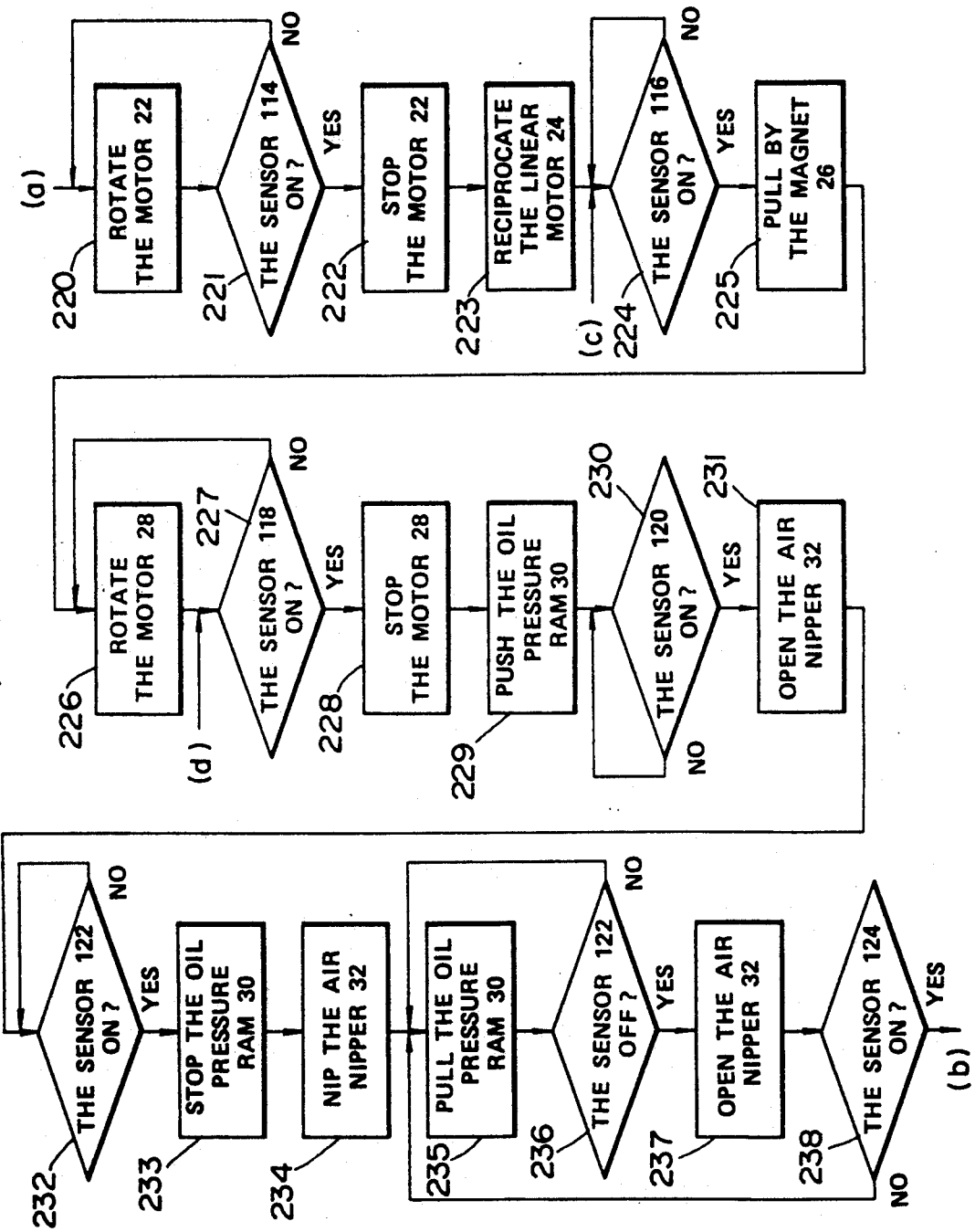

APPARATUS FOR MANUFACTURING HARD CAPSULES FOR MEDICAMENT USE

This is a continuation of application Ser. No. 07/114,715 filed Oct. 30, 1987, now abandoned, which in turn is a Rule 60 divisional application of application Ser. No. 07/046,433, filed May 6, 1987 now abandoned.

This invention relates to manufacturing equipment suitable for mass-production of hard capsules for medicament use.

Gelatin has been used as a thermo-gelling material of hard capsules for medicament use. However, the gelatin has problems in that it may interact with medicament ingredients and in that the control of the moisture content of capsules is troublesome for storage and handling thereof.

With an object to overcome the above described disadvantages of gelatin-made capsules, there have been proposed methods in which cellulose ether substituted with alkyl groups or hydroxyalkyl groups is melted by heat and shaped, and in which molding pins are dipped in a solution of an organic solvent or in an aqueous solution and the solution is shaped by coating the pins with the solution.

The method of melt-shaping with heat has problems in that uniformity of the capsules can hardly be ensured and discoloration into yellow or brown may sometimes take place by the heat during shaping. The method of dipping in the organic solution has a disadvantage in that the solvent, which is toxic to humans, may remain in the capsules, in addition to the troublesome handling of the solvent. In the method of dipping in the aqueous solution, after pulling up the molding pins from the solution, the solution adhering to the pins sags down, so that it is difficult to prepare a capsule of uniform wall thickness. To improve this method it has been proposed to heat the molding pins in advance so that the solution adheres to the surface of the pin in a gelled form. But it is difficult to practice this method, because the effect is insufficient if the heating temperature is too low, while the capsule surface is often wrinkled in the course of drying if the temperature is too high.

The relation to the above-mentioned materials and methods is found in U.S. Pat. Nos. 3,493,407, 4,001,211, 2,810,659, 2,526,683 and 3,617,588.

Machines for making capsules are also found in U.S. Pat. No. 1,787,777.

SUMMARY OF THE INVENTION

The present invention is directed to a method of shaping hard capsules for medicament use having a uniform wall thickness without having wrinkle from an aqueous solution of a cellulose ether.

Therefore, an object of this invention is to provide an improved method of manufacturing hard capsules for medicament use that have a uniform wall thickness, no wrinkle and excellent properties.

Another object of this invention is to provide an improved apparatus for manufacturing hard capsules for medicament use that have a uniform wall thickness, no wrinkle and excellent properties.

A further object of this invention is to provide an improved apparatus which enables mass-production of hard capsules for medicament use.

BRIEF DESCRIPTION OF THE DRAWINGS

The above and further objects and novel features of this invention will more fully appear from the following detailed description when the same is read in connection with the accompanying drawings. It is to be expressly understood, however, that the drawings are for purposes of illustration only and are not intended as a definition of the limits of the invention.

FIGS. 1A and 1B are partially sectional elevation views of a manufacturing apparatus embodying the present invention.

FIGS. 2A and 2B are partially sectional side elevation views of the above apparatus.

FIG. 3 is a partially sectional back side view of the above apparatus.

FIG. 4 is a sectional view taken in the direction of the arrows along the line IV—IV in FIGS. 1A and 3.

FIG. 6 is a perspective view of capsule pins.

FIG. 7 is a sectional view taken in the direction of the arrows along the line VII—VII in FIG. 1A.

FIG. 8 is an illustration of a working condition of a part of the above apparatus.

FIG. 9 is a sectional view taken in the direction of the arrows along the line IX—IX in FIG. 8.

FIG. 10 is a perspective view of air nippers.

FIG. 11 is a top view of an air nippers.

FIG. 12 is a sectional view taken in the direction of the arrows along the line XII—XII in FIG. 9.

FIG. 13 is a drawing illustrating a working condition of a part of the above apparatus.

FIG. 14 is a drawing illustrating the process of coupling a pair of capsules.

FIG. 15 is a sectional view of a greasing device.

FIGS. 17A, 17B and 17C are flow charts of a program of the control system.

DESCRIPTION OF THE PREFERRED EMBODIMENT

The method for manufacturing hard capsules in accordance with the present invention will be explained with reference to the flow chart in FIG. 5.

Figure 5:
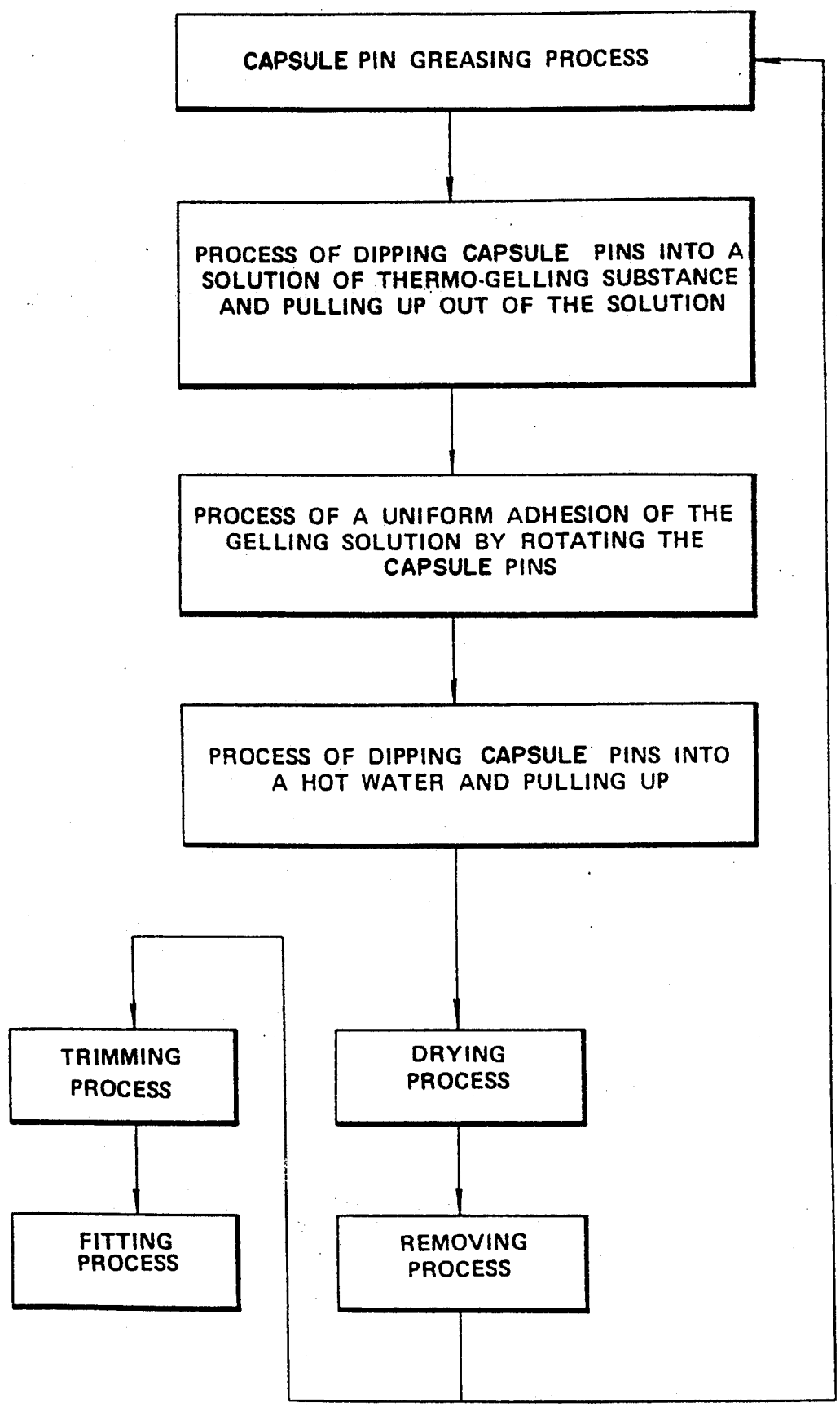
FIG. 5 is a flow chart of method of manufacturing hard capsules.

FIG. 5 shows the following processes: (1) capsule pin greasing, (2) dipping the capsule pins into a solution of thermo-gelling material and pulling them up and out of the solution, (3) uniform adhesion of the gelling solution by rotating the capsule pins, (4) dipping the capsule pins into hot water and pulling them up and out of the hot water, (5) drying, (6) removing, (7) trimming and (8) fitting. The capsule pins pass through from processes (1) to (6), and return to process (1), thus repeatedly circulating through these processes. The manufacturing apparatus is provided with two lines that include processes (1) to (7), which manufacture capsules of different diameters, respectively. A pair of capsules of different diameter are fitted into each other to form a complete capsule.

The above-mentioned solution of the thermo-gelling material preferably provides an aqueous solution capable of being gelled by heating solutions such as alkyl-cellulose, hydroxyalkyl-cellulose and hydroxyalkyl-alkyl-cellulose exemplified by methyl-cellulose, hydroxypropyl-cellulose, hydroxyethyl-methyl-cellulose, hydroxypropyl-methyl-cellulose, hydroxybutyl-methyl-cellulose, hydroxyethyl-ethyl-cellulose, hydroxyethyl-hydroxypropyl-methyl-cellulose and the like are suitable. These cellulose ethers should necessarily be soluble in water so that it is usually desirable that the amount of the substituent groups, i.e. alkyl and hydroxyalkyl groups, is at least 1.4 moles per mole of the glucose units. The viscosity of the aqueous solution prepared thereof is not particularly limitative. A 2%-aqueous solution, which has a viscosity of 2 to 20 centipoise at 20° C., should usually be used for the invention. If the cellulose ether causes the aqueous solution to be of a higher viscosity than above, difficulties are encountered in practicing the inventive method unless the concentration of the dipping solution is decreased.

The cellulose ether is nonionic having no reactivity with medicament ingredients with high safety. Derivatives with ionic substituent groups such as carboxyalkyl groups and the like may react with the medicament eventually to cause denaturation, so that the derivatives cannot be used in the invention.

In practicing the method for the manufacturing of the capsules, the cellulose ether is first dissolved in water in a predetermined concentration. The aqueous solution thus prepared should preferably have a concentration of about 10 to 30% and a viscosity of 1,000 to 15,000 centipoise. The wall thickness of the capsules may be too small if the concentration or viscosity is too low. Difficulties are caused in working if the concentration or viscosity is too high. The aqueous solution is then freed from air bubbles by standing or by subjecting to pressure reduction. This aqueous solution, i.e. dipping solution, is adequately heated and capsule pins are dipped in and kept there for a predetermined length of time followed by pulling up from the solution. The capsule pins are usually at room temperature or may be optionally preheated beforehand to effect fine adjustment of the wall thickness. Thereafter, the coated pins are dipped in water at a higher temperature than the thermo-gelling temperature of the dipping solution so as to effect gelation of the aqueous solution of the cellulose ether. Following the dipping, capsule pins with the gel of cellulose ether are dried up by oven.

The dried capsule portions are demounted from the pins and trimmed into a predetermined size to give a body of the capsule. Separately, the cap of the capsule having a slightly larger diameter than the body is shaped in the same manner. A cap of a capsule and a body of that capsule are fitted into each other, so that a completed capsule for medicament use is obtained. The base material of the capsules may be admixed with other additives according to need. Representative additives include modifiers such as polyvinyl-alcohol, plasticizers such as glycerin, sorbitol, mannitol, sucrose and polyethylene-glycol, light-shielding agents such as titanium-dioxide, barium-sulfate and precipitated-calcium-carbonate and coloring agents such as water-soluble dyes and lake pigment. In order to facilitate demounting of the shaped form of capsule from the pin, the pin may be coated with a mold-release agent such as cotton seed oil, liquid paraffin and the like.

A preferred embodiment in accordance with the present invention is shown in FIGS. 1A, 1B, 2A, 2B, 3 and 4. These drawings show only one of the two lines used to form (1) the capsule cap and (2) the capsule body. The two lines are generally constructed in mirror image to each other, and the dimensions of the capsule pins differ a small amount between the two lines, so that capsules of one line fit into capsules of the other line to form completed capsules. Therefore, by the detailed description of one line, the details of the other line will be also understood.

FIGS. 1A(IA—IA) and 1B (IB—IB) are partial sectional elevation views of the apparatus, which connect to each other and are views taken in the direction of the arrows along the line IA·IB—IA·IB in FIGS. 2A and 4. FIGS. 2A (IIA—IIA) and 2B (IIB—IIB) connect to each other and are partially sectional side elevation views taken in the direction of the arrows along the line IIA·IIB—IIA·IIB in FIGS. 1B and 3. FIG. 3(III—III) is a view taken in the direction of the arrow along the line III-III in FIGS. 2B and 4. FIG. 4 (IV—IV) is a view taken in the direction of the arrows along the line IV—IV in FIGS. 1A and 3. A plan layout of units shown in these figures forms an approximate quadrilateral, respective sides of which correspond to units shown in FIGS. 1A and 1B, FIGS. 2A and 2B, FIG. 3 and FIG. 4. Capsule pins form capsules while circulating along these quadrilateral sides.

Two or more capsule pins 2 are arranged and fixed on a base plate 50 as shown in FIG. 6. Each of pins 2 has a smoothly finished surface and a hemi-spherical tip. The pins 2 may be plated to give a smooth surface. The base plates 50 are made of corrosion-resistant magnetic such as magnetic stainless steel or plated steel.

Though there is no specific starting point nor end point of capsule pins 2 in the processes because the capsule pins 2 are always circulating to continuously produce capsules 1, the description is started from the means to dip capsule pins 2 after greasing into the gelling solution.

As shown in FIG. 1A, a pair of guide benches 51 supports base plates 50 on the bottom face at the front and back sides of FIG. 1A, and each capsule pin 2 is positioned so that its tip is kept downside. An air piston 10 is arranged to push the base plates 50 standing in this position. A guide bench 51 is equipped with a sensor 102 to detect the base plate 50.

An elevator 5 is adjacently arranged to the guide benches 51. The elevator 5 is driven by a linear motor 12 mounted on an upper chassis 48, whose drive shaft 55 is connected with the elevator 5. The body of the elevator 5 is a box type, whose left, right and bottom sides are open. The elevator body has down-juts 56 which are angled boards attached to the lower parts of the front and back sides of the box. The down-juts support base plates 50 at the front and back sides of FIG. 1A. The elevator 5 can support five base plates 50. When the elevator 5 is in the position shown in FIG. 1A, i.e. home position, base plates 50 with the pins 2 can be moved onto the down-juts 56 by the pushing action of a plunger 53 of air piston 10. A tank 4 arranged under the elevator 5 is filled with a dipping aqueous solution 3 of a thermo-gelling non-ionic cellulose ether, i.e. gelling material. The tank 4 is provided with an electric heater 58 and a thermo-couple 59, which are connected to a thermo-controller 200, and with a magnetic stirrer 60 serving to stir the solution 3, thus keeping constant temperature of the solution 3. The thermo-controller 200 may be a well known control system such as PID control. The tank 4 is equipped with a sensor 104 for detecting the elevator 5. Under such conditions, capsule pins 2 are dipped into and taken out from the dipping solution 3.

A linear motor 14 is mounted on the upper chassis 48 and push rods 62a and 62b are supported on a drive shaft 62 of linear motor 14. The push rods 62a and 62b are fitted with a stopper 63, respectively, so that they can swing clockwise but not counterclockwise. The home position of drive shaft 62 is shown with solid lines in FIG. 1A, whose tip is positioned near the center of the elevator 5. One end of the push rod 62a is in contact with a pin plate 50 which is nearest one of base plates 50 in the elevator 5 to the guide benches 51.

A revolving cylinder 11 is arranged close to the elevator 5. It is provided, as shown in FIG. 7 (sectional view VII—VII), with two grooves 11a and 11b which are opposite one another on the inside wall of the cylinder 11 to support base plates 50 with pins 2. The revolving cylinder 11 is held at the outer surface by a revolvable bearing device 65, and a peripheral gear 66 of the cylinder is meshed with a drive gear 67 of a motor 16. In such condition as shown in FIG. 1A, the faces of grooves 11a and 11b that support base plates 50 are flush with the upper surface of down-juts 56 when the elevator 5 is in its home position. When the push rod 62a pushes base plates 50 in the elevator 5, the base plates 50 slide along into the revolving cylinder 11. By rotation of capsule pins 2 in the cylinder 11, the process of uniform adhesion of the gelling solution to the pins 2 is conducted.

As shown in FIG. 1B, an elevator 7 is arranged close to the revolving cylinder 11, in connection with drive shaft 69 of a linear motor 18 mounted on the chassis 48. The shape of the elevator 7 is the same as that of the elevator 5 which has been already described. When the elevator 7 is in its home position as shown in FIG. 1B, the top faces of the down-juts 70 of the elevator 7 are flush with the faces of the grooves 11a and 11b of the revolving cylinder 11 which support base plates 50 with pins 2 so that the pushing action of the push rod 62b slides the base plates 50 into the elevator 7. A sensor 106 is fitted at the end of the elevator 7 to detect the push rod 62b, and a hot water vessel 6 is located under the elevator 7. An electric heater 72 and a thermo-couple 73 connected with a thermo-controller 199, and a magnetic stirrer 75 are installed inside the vessel 6 to keep constant the temperature of the hot water. A sensor 108 to detect the elevator 7 is also fitted to the vessel 6. In this section, cupsule pins are dipped into and taken out from the hot water, and thus gelation of the solution adhering to the capsule pins is accelerated, forming capsules.

A belt conveyor 77 is arranged adjacent to the elevator 7, on which carrying frames 78 can ride. The carrying face of the frame 78 is flush with the top faces of the down-juts 70 of the elevator 7 so that base plates 50 with pin 2 can be transferred from the elevator 7 onto a carrying frame 78 by a hooked bar 81 fitted to shaft 80 of a linear motor 20. A sensor 112 is installed at an unmoving part of the belt conveyor 77 to detect a carrying frame 78.

As shown in FIGS. 2A and 2B, carrying frames 78 with base plates 50 on the belt conveyor 77 pass through a drying chamber 8. The drying chamber 8 is provided with pipes 82 which have a number of holes on their side faces, and through which dry air at a temperature of about 50° C. is blown into chamber 8 for drying. The belt conveyor 77, driven by a motor 22, carries carrying frames 78 from point P shown in FIG. 2A to point Q in FIG. 2B. A sensor 114 detects arrival of base plates 50 on the frame 78 at point Q. Once the base plates 50 are transferred from point P to point Q, the base plates have to be unloaded from the carrying frame 78 by a means described below, and the carrying frame 78 returned from point Q to point P. For returning the carrying frame 78 another conveyor may be installed to fix carrying frames 78 onto belt conveyor 77 and provide under the belt conveyor 77 a large enough space to pass carrying frames 78, or to return manually the carrying frames 78.

As shown in FIG. 3, by the pushing action of a shaft 83 of a linear motor 24, a base plate 50 with pins 2 placed on carrying frame 78 runs down one by one on an inclined roller conveyor 84. In the condition shown in FIG. 3, an electromagnet 26 holds a base plate 50 and stops its forward movement. Then once electromagnet 26 with the base plate 50 is turned back by a means described below, the next base plate 50 is placed on a fixed stand 85 and checked by a stopper 86. The fixed stand 85 is equipped with a sensor 116 to detect a base plate 50. Above the fixed stand 85, two turning plates 88 with a common shaft 88a are arranged with a space approximately equal to the length of a base plate 50. Turning plates 88 are driven by a motor 28. In a space between them an electro magnet 26 is fitted to bridge both plates 88. When the electromagnet 26 comes down to the lowest level by turning the plates 88, it picks up a base plate 50 from the fixed stand 85, and is turning soon thereafter. Furthermore, sensors 128, 118 and 126 are arranged to detect the electromagnet 26 in the lowest, highest (½ turn) and middle positions on the right side (¾ turn), respectively. When electromagnet 26 comes down to the lowest position, it pulls a base plate 50. While turning together with turning plates 88, the electromagnet 26 brings the base plate with pins 2 to the highest position. In this position, a formed capsule is removed from the capsule pins.

Means for removing, trimming and fitting the capsules are arranged above turning plates 88.

The means for removing capsules includes an oil pressure ram 30 and two pairs of air nippers 32. When oil pressure ram 30 is pulled into the cylinder 30a, a swinging part 91 is pulled by the ram 30 through a spring 90, and a link bar 93 which turns as a whole with the swinging part 91, comes in contact with a stopper 92, and thus the swinging part 91 is positioned perpendicularly to ram 30. The ram 30 is pushed out from the cylinder 30a and comes down. The swinging part 91 is pushed by the counteraction of the link bar 93 held against stopper 92, and the swinging part 91 also begins to swing counterclockwise against the pulling-back force of the spring 90. As soon as the swinging part 91 swings beyond a critical position relative to swinging axis 95, the swinging part 91 is abruptly swung by the pulling force of the spring 90, so that the link bar 93 hits against a stopper 96 and is positioned in line with the ram 30. A sensor 120 detects this alignment of link bar 93 and the ram 30. Upon the detection of the alignment, the ram 30 comes down gradually and stops at a given position. When the ram 30 stops, a base plate 50 with pins 2 carried by the turning plates 88 has just come to the highest level of the turning plates 88. This condition is shown in FIG. 8. It is detected by a sensor 122 that the ram 30 has come down to position.

FIG. 9 shows a view taken in the direction of the arrows along the line IX—IX in FIG. 8. As shown in this figure, the turning part 91 fits with a frame 98 equipped with air nippers 32. As shown in FIG. 10, nipping bars 32a and 32b of the nippers 32 have semicircular cuts, the inner diameter of which fits the outside diameter of capsule pins 2. FIG. 10 shows the state where the air nippers 32 are kept released from air pressure so that the nipping bars 32a and 32b have opened, i.e. separated from each other. When the ram 30 stops at a given position, and compressed air is introduced into nippers 32, the nipping bars 32a and 32b close and nip capsule pins 2 near their root. A bird's-eye view of this condition within the limits of nippers 32, capsule pins 2 and some related parts is shown in FIG. 11. As shown in FIG. 9, frame 98 is equipped with an oil pressure cylinder 34a and a female die 38. The oil pressure ram 34 of the oil pressure cylinder 34a is provided with plungers 40 aligned at the same pitch as that of the capsule pins 2 on a base plate 50. A female die 38 has holes arranged also at the same pitch as the capsule pins 2. The cross section along the line XII—XII is detailed in FIG. 12. The diameter of the holes of female die 38 changes at mid-depth from larger to smaller. Larger hole 38a has such a diameter that a capsule pin 2 to which dried capsule still adheres fits closely to hole 38a, and small hole 38b has such a diameter that a plunger 40 can loosely pass through hole 38b. As shown in FIG. 12, the nipping bars 32a and 32b slidably hold the capsule pins 2 at a part of pin 2 to which dried capsule is not adhering (near the base plate 50). Therefore, if the frame 98 is lifted vertically from the state as shown in FIG. 12, capsules 1 are kept fitted closely to the female die 38, and are removed from capsule pins 2, thus completing the capsule removing process.

If, starting from the state as shown in FIG. 8, the oil pressure ram 30 moves up and accordingly the swinging part 91 rises vertically, capsules 1 held in female die 38 are removed from the capsule pins 2 and then the air nippers 32 are opened. As the swinging part 91 rises, a slant 93a of the link bar 93 comes into contact with and is pushed by a guide pin 41, so that link bar 93 swings clockwise against the pulling-back force of the spring 90. As soon as the link bar 93 swings beyond a critical position relative to swinging axis 95, the swinging part 91 is abruptly swung by the pulling-force of the spring 90, so that link bar 93 hits against a stopper 92 and is positioned perpendicularly to the ram 30. A partial sectional view of the above condition is shown in FIG. 13. This condition is detected by a sensor 124. A cutter knife 43 is arranged close to the swinging locus of the face of female die 38, and an end 1a of capsules 1 is cut by swinging the die 38. Thus, capsules 1 are trimmed and of a uniform length.

In the condition where female die 38 has swung as described above (see FIG. 13), a coupling die 44 is arranged close to the female die 38. The coupling die 44 has through holes and the inside of one of them is stepped to different diameters in the middle of the hole. The diameter of a smaller-diameter part 44a of the hole is so large that a capsule 1 can slide inside the part 44a. The diameter of a larger-diameter part 44b of the hole is so large that the part 44b can be fitted with a capsule 100 which has slightly larger outer diameter than that of a capsule 1 and is manufactured using the other line of the apparatus. As described above, the other line is a mirror image of that for manufacturing capsules 1. Coupling die 44 holds capsules 100 manufactured through the processes as described above. The coupling die 44 is provided with a sensor 130 to detect whether capsule 100 is correctly held in a hole of die 44. In this condition, the ram 34 is pressed down from the cylinder 34a, the plunger 40 pushes capsules 1 to make each capsule 1 fit into a capsule 100, and the coupled capsules 1 and 100 are then pushed out of coupling die 44 as shown in FIG. 14.

As shown in FIG. 3, after capsules 1 are removed from the capsule pins 2 of the base plate 50, when the electromagnet 26 mounted on the turning plates 88 comes to the top position, turning plates 88 turn further by ¼ turn relative to base plate 50 so that electromagnet 26 faces to the right side and the base plate 50 faces to a holder 45. The receiving face of the holder 45 is set only at the sections corresponding to both end parts of the base plate 50 so as not to interrupt the turning of capsule pins 2 (see FIG. 4). The electromagnet 26 stops pulling at this step. A linear motor 36 is arranged to be push the base plate 50 in this state. By the pushing action of the linear motor 36, the base plate 50 is pushed out from the holder 45 and passes through a slide rail 46, a greasing device 47 and another slide rail 49. At the end of slide rail 49, a falling guide way 54 and, thereunder, a pair of guide benches 51 are arranged (see FIG. 1A). As shown in FIG. 15, greasing device 47 has soft brushes 57 in the space through which capsule pin 2 passes, and tubes 61a and 61b circulate grease to facilitate removal of capsule 1 from capsule pin 2. It is preferable that the grease is e.g. liquid paraffin, edible oil or silicone oil.

Figure 16:
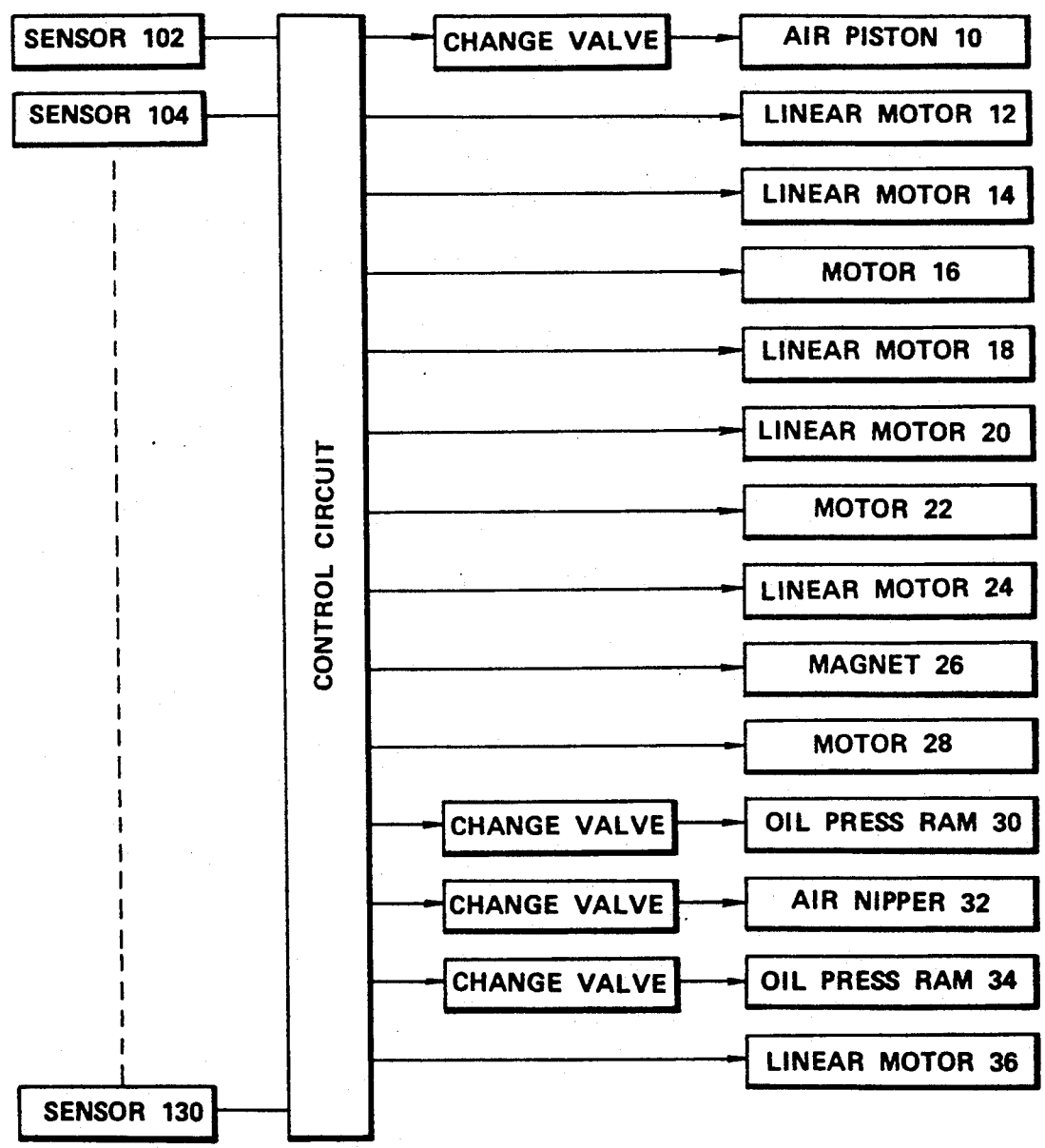
FIG. 16 is a schematic block diagram of a control system in the above apparatus.
Figure 17A:
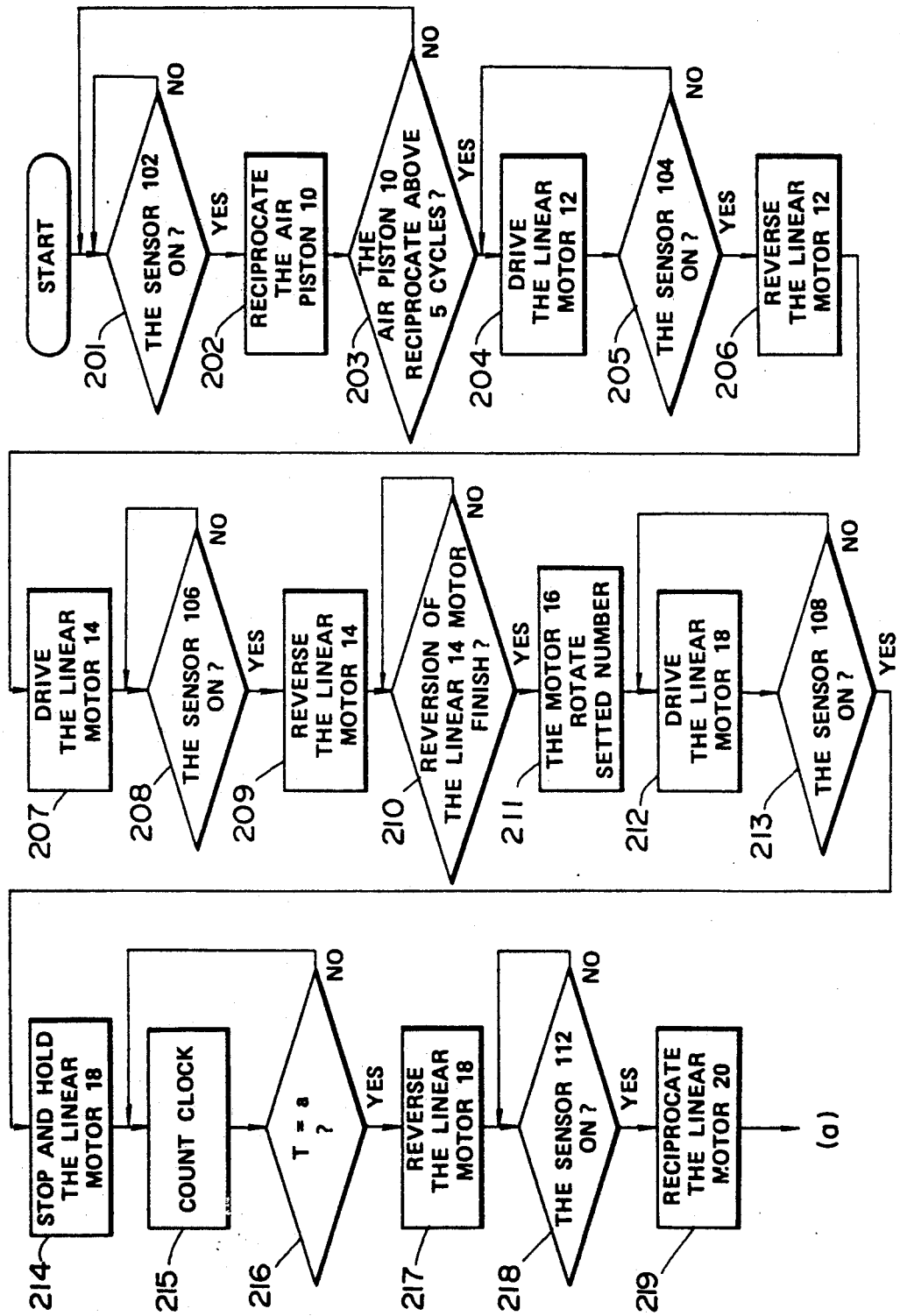
Figure 17C:
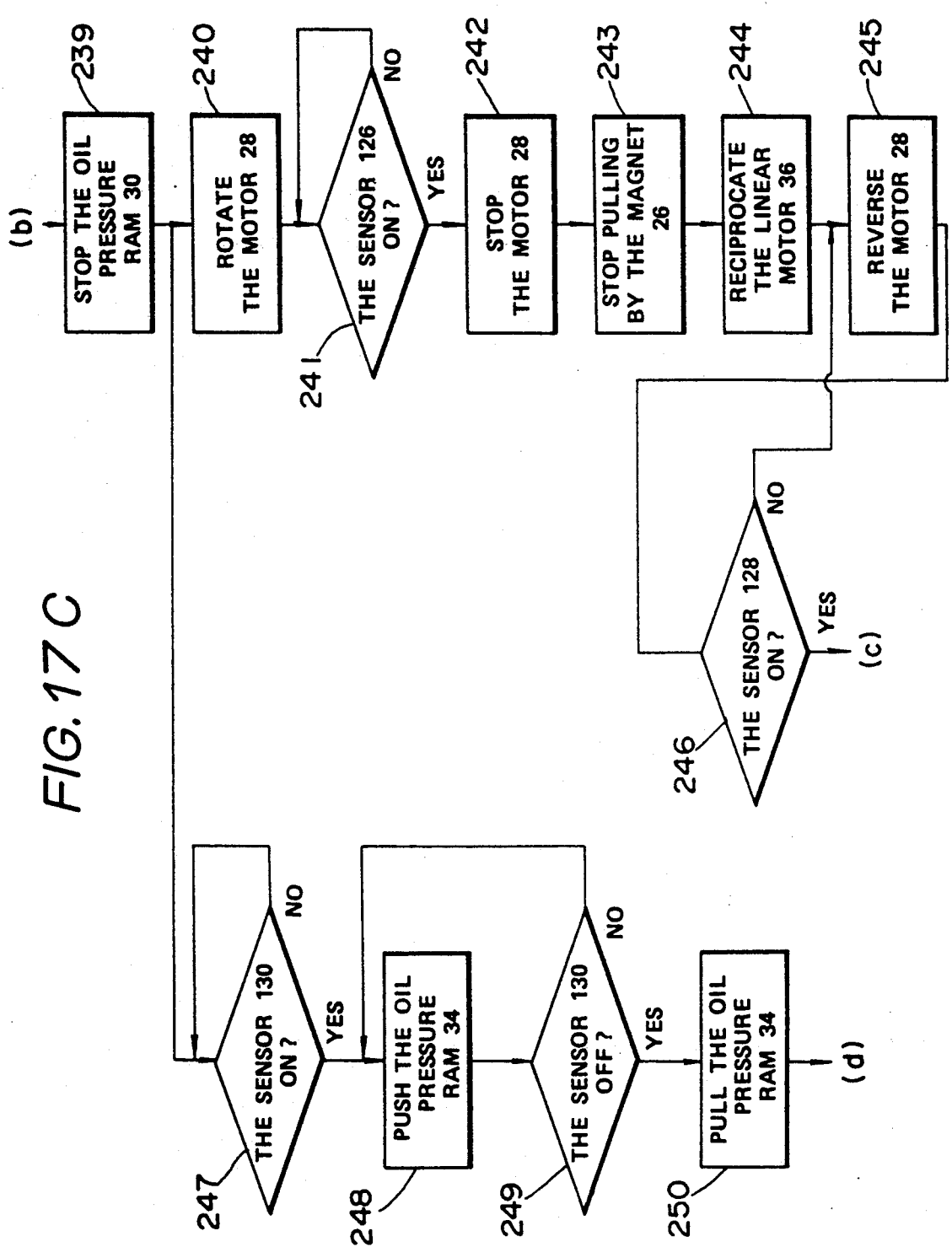

The control system for the above-mentioned apparatus, shown as a schematic block diagram in FIG. 16, drives respective drive devices 10 to 30 while detecting timing by sensors 102 to 130. The programs shown in the flow charts of FIGS. 17A, 17B and 17C are stored in the read only memory (ROM) area of the control circuit of the block diagram. The operation control of steps 201 to 250 is conducted according to the procedure illustrated in the flow charts.

Upon start of the control system, a sensor 102 detects the presence of a base plate 50 (201). If not, the system stays in a state of waiting. If the presence of a base plate 50 is detected, an air piston 10 enters into reciprocating motion (202). Every time the piston 10 reciprocates, one of the base plates 50 is delivered to an elevator 5. After five reciprocating cycles of the air piston 10 (203), a linear motor 12 is driven once to advance (204). When a sensor 104 detects completion of dipping capsule pins 2 into a gelling solution 3 (205), a linear motor 12 is reversed (206). Then a linear motor 14 is advanced (207). If a sensor 106 detects the presence of a push rod 62b (208), this detection tells that by the pushing action of the push rod 62a, five base plates 50 have been transferred into a revolving cylinder 11. Upon the detection of the push rod 62b, the linear motor 14 is driven to reverse (209), and reversion of the motor 14 is ascertained (210), so that the push rod 62b does not prevent the subsequent operation.

In the subsequent step, a specified number of rotations of motor 16 (211) causes the revolving cylinder 11 to revolve only one cycle. Due to the advancing motion of the linear motor 14 in step 207, the rod 62b has pushed the base plates 50 kept in the cylinder 11 into an elevator 7, an advancing motion of a linear motor 18 (212) dips capsule pins 2 into hot water in a vessel 6. When sensor 108 detects dipping of capsule pins 2 (213), the linear motor 18 is immediately stopped and the capsule pins 2 are held in the hot water for a preset period of time "a" (214) to ensure sufficient penetration of heat into the capsule pins. Just when the count of time T of a clock built in the control circuit reaches "a" (215) (216), the linear motor 18 is reversed (217) to move up the elevator 7. On the other hand, after sensor 112 checks that a carrying frame 78 is in position on a belt conveyor 77 (218), a linear motor 20 is reciprocated (219) to transfer base plates 50 from elevator 7 onto carrying frame 78 by a hooked bar 81.

Then, as shown in FIG. 17B, by rotating a motor 22(220) the belt conveyor 77 transfers the carrying frame 78 loaded with base plates 50 through a drying chamber 8. When a sensor 114 detects a base plate 50 (221), motor 22 stops, and consequently the belt conveyor 77 stops (222). A linear motor 24 is then reciprocated to transfer the base plates 50 onto rollers 84 (223). Then a sensor 116 detects arrival of a base plate 50 from the rollers 84 (224) and an electromagnet 26 pulls the base plate 50 (225). In this condition a motor 28 rotates in a normal direction (226) and, on detection of the electromagnet 26 by a sensor 118 (227), the motor 28 stops (228). At this time the base plates 50 are positioned at the top of turning plates 88. Then, an oil pressure ram 30 is pushed (229), and a swinging part 91 begins to swing and eventually aligns with the ram 30. This alignment is detected by a sensor 120 (230), and upon the detection, two pairs of air nippers 32 open (231). When a sensor 122 detects a finale die 38 (232), the oil pressure ram 30 stops (233). At this time the air nippers 32 close (234). Then the ram 30 begins to be pulled (235) and capsules are removed from capsule pins 2. When the ram 30 comes out of the detection of the sensor 122 (236), nippers 32 are released to open (237). When sensor 124 detects that swinging part 91 has swung 90° to its home position (238), the control shifts to the process shown in FIG. 17C., and the ram 30 stops (239).

Here, a motor 28 rotates in the normal direction (240) and, upon detection of the base plate 50 by a sensor 126 (241), the motor 28 stops (242), to face the base plate 50 toward a holder 45. Then, the electromagnet 26 stops pulling (243) and a linear motor 36 reciprocates one cycle (244), the base plate 50 with capsule pins 2 comes back to the starting position (position detected at the step 201) through a greasing device 47. After the linear motor 36 reciprocates one cycle at the step (244) a motor 28 rotates reversely (245), and upon detection of the presence of electromagnet 26 by a sensor 128 (246), the operation returns to the step 224. These operations are repeated.

After an oil pressure ram 30 is stopped at step 239, and if it is detected by a sensor 130 that a capsule 100 is correctly fitted into a coupling die 44 (247), an oil pressure ram 34 is pushed (248). It is confirmed by discontinuation of signal output from the sensor 130 (249) that capsule 100 with capsule 1 has fallen off from coupling die 44. Then the ram 34 is pulled back (250). Thus the operation returns to the step 227. These operations are repeated.

To make it easy to understand the procedure of each process, the program in the above description is of a serial control. However parallel controls are also applicable to the control system of this invention. For instance, the downward motion of an elevator 5 by a linear motor 12 and that of an elevator 7 by a linear motor 18 may be conducted in parallel controls.

The invention will be more clearly understood with a reference to the following examples:

EXAMPLE 1

A dipping solution was prepared by dissolving hydroxypropyl-methyl-cellulose comprising 10 weight % hydroxypropoxyl groups and 29 weight % methoxyl groups of a 2% aqueous solution having a viscosity of 6 centipoise at 20° C., in water in a concentration of 22% followed by standing overnight and removing of bubbles under vacuum. Pins for #3 capsule coated beforehand with liquid paraffin were dipped in this dipping solution, warmed at 40° C. and pulled up out of the solution. After the drop at the pin heads had dripped, the pins were turned upside down and kept standing for 25 seconds. The pins were then dipped in hot water at 85° C. for 10 seconds and transferred into a drying oven kept at 55° C. where they were kept for 30 minutes, so that the gelled solution was dried up to give a shaped form of capsules. The shaped forms were removed from the pins and trimmed into a predetermined size to give capsule bodies. Thus prepared capsule bodies were free of wrinkle and had a uniform wall thickness of 0.12 mm at the head and 0.10 to 0.11 mm at the cylindrical trunk. Caps were prepared in the same manner as above. After filling with starch, a pair of body and cap was put into each other to give a capsule, the capsule was subjected to the disintegration test according to the procedure specified in the 11th Revised Japanese Pharmacoeia, and the disintegration time was 6.5 minutes.

EXAMPLE 2

A dipping solution having a solid content of 22% was prepared by blending a 22.2% aqueous solution of 100 parts of the above Example 1. Hydroxypropyl methyl cellulose and a dispersion of 2 parts of titanium dioxide (A-110, product by Sakai Chemical Co.) in a calculated amount of water followed by standing overnight and removal of bubbles under vacuum. Subsequently, a capsule containing a light-shielding agent was prepared in the same manner as in Example 1. The capsules were free of wrinkle and had a uniform wall thickness. The disintegration time thereof was 6.0 minutes as determined in the same manner as in Example 1.

EXAMPLE 3

An aqueous solution having a solid content of 18% was prepared by dissolving 97 parts of a hydroxypropyl methyl cellulose comprising 5 weight % hydroxypropoxyl groups and 28 weight % methoxyl groups, respectively, and a 2% aqueous solution having a viscosity of 12 centipoise at 20° C. and 3 parts of a polyvinyl alcohol having a degree of saponification of 88 mole % and 5 centipoise viscosity of 4% aqueous solution at 25° C., in water and after standing overnight. The solution was freed of bubbles under vacuum to give a dipping solution. Capsule pins for #3 capsule coated with liquid paraffin and heated at 50° C. beforehand were dipped in the dipping solution kept at room temperature followed by the same procedure as in Example 1 to give capsules. The capsules were free of wrinkle and had uniform wall thickness. The disintegration time thereof was 9.5 minutes.

EXAMPLE 4

A dipping solution was prepared by dissolving a hydroxypropyl cellulose comprising 63 weight % hydroxypropoxyl groups having a viscosity of 6 centipoise in a 2% aqueous solution at 20° C., in water in a concentration of 21% followed by standing overnight and removing of bubbles under vacuum. Capsule pins for #3 capsule coated with liquid paraffin beforehand were dipped in the dipping solution followed by the same procedure as in Example 1 except that the temperature of the hot water was 70° C. to give capsules. The capsules were free of wrinkle and had uniform wall thickness. The disintegration time thereof was 6.0 minutes.

While the invention has been particularly shown and described with reference to preferred embodiments thereof, it will be understood by those skilled in the art that the foregoing and other changes in form and details can be made without departing from the spirit and scope of the invention.

What is claimed is:

1. An apparatus for manufacturing water-soluble hard capsule bodies or capsule caps for medicament use, comprising:

means for circulating sets of capsule pins fixed on plates through the apparatus;

greasing devices for greasing said capsule pins;

tanks filled with a solution of thermo-gelling material;

means for dipping and removing said greased capsule pins from the solution in said tanks;

means for revolving said capsule pins coated with the solution by at least one rotation;

vessels filled with hot water thermally controlled at a higher temperature than the gelling temperature of the solution, thereby effecting gelation of the solution and producing a wrinkle-free coating of uniform wall thickness of the solution of said capsule pin;

means for dipping and removing said coated capsule pins from said vessels;

drying devices for drying solvent from the solution adhering to said capsule pins after removal from said vessels;

means for removing said capsule bodies or said capsule caps formed of the dried thermo-gelling material from said capsule pins;

trimming devices for trimming said dried capsule bodies or said dried capsule caps;

a fitting device for fitting said capsule bodies into said capsule caps.

2. The apparatus of claim 1, wherein said circulating capsule pins are transferred by a linear motor from said tanks to said means for revolving and from said means for revolving to said drying devices.

3. The apparatus of claim 1, wherein said greasing devices are soft brushes which continuously supply grease to said capsule pins and are arranged such that the circulating capsule pins pass therethrough.

4. The apparatus of claim 1, wherein said means for revolving are revolving cylinders whose insides each have two grooves to support said plates which fix the capsule pins thereon.

5. The apparatus of claim 1, wherein said drying devices are chambers which blow dry air, said capsule pins coated with said solution being transferred therethrough while keeping an upward orientation.

6. The apparatus of claim 1, wherein said means for removing said capsule bodies or said capsule caps are air nippers of which nipping bars nip roots of said capsule pins and then pull said capsule bodies or said capsule caps from said capsule pins.

7. The apparatus of claim 1, wherein said trimming devices are cutter knives arranged to cut ends of said capsule bodies or said capsule caps moving from said means for removing said capsule bodies or said capsule caps to said fitting device.

* * * * *